United States Patent [19]

Kopito et al.

[11] 4,131,112
[45] Dec. 26, 1978

[54] PROBE FOR OBTAINING SAMPLE OF CERVICAL MUCUS

[75] Inventors: Louis Kopito, Brookline; Samuel R. Schuster, Wellesley; Harold Kosasky, Brookline, all of Mass.

[73] Assignee: Ovutime, Inc., Brookline, Mass.

[21] Appl. No.: 753,007

[22] Filed: Dec. 21, 1976

[51] Int. Cl.² .................. A61B 10/00; A61M 1/00
[52] U.S. Cl. ............................ 128/2 B; 128/234; 128/278
[58] Field of Search ............... 128/2 W, 2 B, 2 F, 278, 128/276, 277, 218 C, 218 P, 234; 73/425.4 P, 423 R, 425.6

[56] References Cited

U.S. PATENT DOCUMENTS

| | | | |
|---|---|---|---|
| 1,381,774 | 6/1921 | Weiner | 128/234 |
| 3,147,753 | 9/1964 | Nogier | 128/218 P |
| 3,554,185 | 1/1971 | Kohl | 128/2 B |
| 3,738,539 | 6/1973 | Beich | 128/234 |
| 3,890,956 | 6/1975 | Moorehead | 128/2 F |
| 4,022,207 | 5/1977 | Citrin | 128/218 C |

*Primary Examiner*—Dalton L. Truluck
*Assistant Examiner*—V. Millin
*Attorney, Agent, or Firm*—Morse, Altman, Oates & Bello

[57] ABSTRACT

A probe, for obtaining a sample of an oftentimes minute in vivo quantity of cervical mucus, comprises a syringe-like structure characterized by an apertured specimen cavity of variable size that is defined by an outer barrel and an inner plunger of particular configurations capable of producing relative peristaltic motion. The forward end of the barrel, which is rigid, has a forward opening which communicates with a relatively deep internal concave surface. The forward end of the plunger, which is elastomeric, has a relatively shallow external convex surface that deforms as the plunger reciprocates. As the plunger moves forwardly, the external increments of its convex surface are deformed in such a way as to completely fill the specimen cavity and to ensure that even minute amounts of cervical mucus inducted into the specimen cavity through the forward opening can be ejected completely from the specimen cavity through the forward opening when desired.

3 Claims, 7 Drawing Figures

PROBE FOR OBTAINING SAMPLE OF CERVICAL MUCUS

BACKGROUND OF THE INVENTION

1. Field of the Invention

The present invention relates to the retrieval of cervical mucus in vivo and, more particularly, to probes for insertion through the vaginal cavity into contact with the cervix in order to retrieve a specimen of cervical mucus from the cervical os without contamination by other vaginal fluids.

2. The Prior Art

Efforts have been made to retrieve cervical mucus in vivo at various phases of the menstrual cycle for, among other purposes, testing as an indicator of fertility. Difficulties have been encountered in retrieving the specimens during phases of the menstrual cycle during which the amount of cervical mucus available is exceedingly minute.

SUMMARY OF THE INVENTION

The object of the present invention is to provide a probe, for obtaining a sample of an oftentimes mintute in vivo quantity of cervical mucus, which comprises a syringe-like structure characterized by an outer barrel and an inner plunger of particular configurations capable of producing relative peristaltic motion. The forward end of the barrel, which is rigid, has a forward opening which communicates with a relatively deep internal concave surface. The forward end of the plunger, which is elastomeric, has a relatively shallow external convex surface that deforms as the plunger reciprocates. The cooperating forward configurations of the outer barrel and the inner plunger define therebetween the specimen cavity which: (1) when it is caused to increase in volume with rearward motion of the plunger, receives a fluid specimen through the forward opening under suction; and (2) when it is caused to decrease in volume with forward motion of the plunger, ejects the fluid specimen through the forward opening under pressure. As the plunger moves forwardly, the external increments of its convex surface are deformed in such a way as to completely fill the specimen cavity and to ensure that even minute amounts of cervical mucus inducted into the specimen cavity through the foward opening during retrieval can be ejected completely from the specimen cavity through the forward opening when desired.

Other objects of the present invention will in part be obvious and will in part appear hereinafter.

The present invention thus comprises the devices, together with their components and interrelationships, which are exemplified in the present disclosure, the scope of which will be indicated in the appended claims.

BRIEF DESCRIPTION OF THE DRAWINGS

For a fuller understanding of the nature and objects of the present invention, reference is made to the following detailed description, taken in connection with the accompanying drawing, wherein.

SUMMARY OF THE INVENTION

The viscosity of cervical mucus varies greatly through the menstrual cycle. At mid-cycle, the mucus is watery and abundant and relatively easy to retrieve to enable chemical and physical testing for diagnostic purposes. The quantity of mucus produced at mid-cycle may amount to 200 to 700 milligrams. This mucus in physical appearance resembles egg white; being clear, elastic and free of cellular material. During the immediate pre and post menstrual phases (the proliferative and luteal phases), the cervical mucus undergoes significant changes in appearance, physical properties and quantity. The mucus is relatively dehydrated and of heterogenous composition. It contains over ten times as much protein as mid-cycle mucus and is infiltrated with cast off epitheleal cells from the cervix. At these times, the mucus does not flow freely and may have the consistency of glue or rubber cement. The retrieval of representative specimens for diagnostic analysis has been difficult if not impossible. Furthermore, the amount of mucus, which is available at the immediate post and pre menstrual phases is very small, on the order of less than 5 to 30 milligrams.

A commonly used present procedure for sampling cervical mucus consists of inserting into the cervical os a one millimeter tuberculin syringe (without the needle) and gathering the available mucus by air suction. This procedure, while satisfactory when mucus in available in great abundance, is of little value during most of the menstrual cycle, i.e. at times other than the time of ovulation plus or minus two or three days. The reasons for this are:

(1) air pressure produced by the descending plunger of the syringe usually is insufficient to force out the viscous glue-like mucus; and (2) the relatively small amount of available mucus may be retained in a dead space in the front end of the syringe. This dead space is located in the projectin that normally serves to hold the needle.

DETAILED DESCRIPTION OF THE PREFERRED EMBODIMENT

Figure 1:
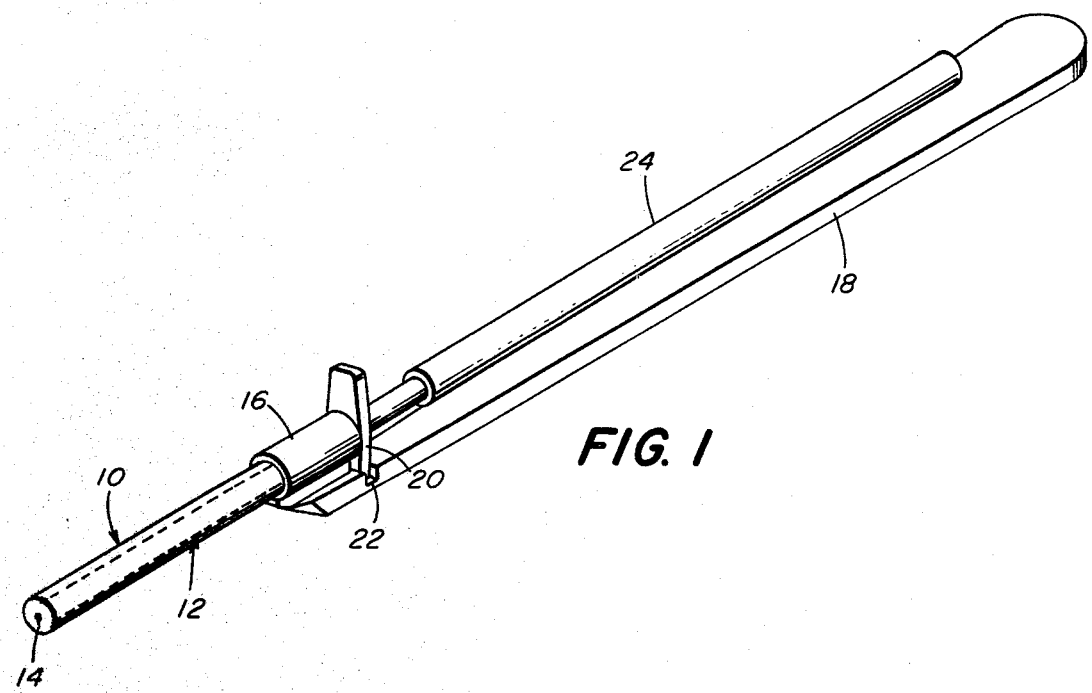
FIG. 1 is a perspective view of a device embodying the present invention.

The embodiment of the present invention illustrated in FIG. 1 comprises an outer barrel 10 and an inner plunger 12, which are relatively reciprocial in telescoping relation. The external surface of the main body of the plunger and the internal surface of the main body of the barrel are of approximately the same diameter with slight clearance to permit relative reciprocation. Barrel 10 has a forward aperture 14 and is supported within a circular mount 16 at the forward end of a handle 18. Barrel 10, after being inserted through circular mount 16 is prevented from moving with respect to handle 18 by a key 20, which is affixed to the rearward end of the barrel and which can be engaged with and disengaged from a slot 22 in handle 18. Key 20 has an opening in registration with the cross sectional opening of barrel 10. Thus barrel 10 and plunger 12 are sterilized disposable parts that, before use, are stored in a sterilized packet. Plunger 12 extends rearwardly fron the interior of barrel 10 through the region of circular mount 16 and key 20. The rearward end of plunger 12 is press fitted into a handle 24, which is approximately the same length as handle 18. These handles permit the forward ends of the barrel and the plunger to be inserted through the vaginal cavity into proximity with the cervical os and at the same time to be controlled externally by the hands of a physician. Preferably, both barrel 10 and plunger 12, except for its forward tip, are composed of a polymeric material such a polymethyl methacrylate or a vitreous material such as glass. Preferably, the forward tip of plunger 12 is composed of an elastomeric material such as natural or synthetic rubber. Preferably handles 18, 24 are composed of a polymeric material such as polymethyl methacrylate.

Figures 2A, 2B, 2C:
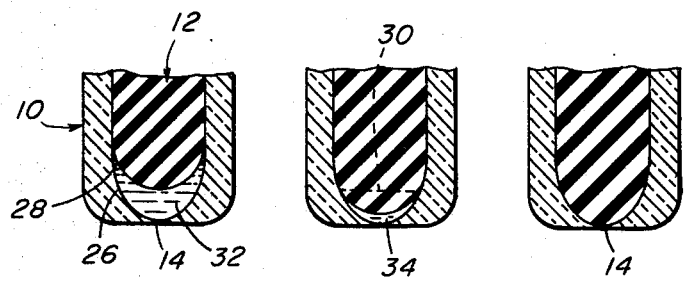
FIGS. 2A, 2B, 2C are a sequence of cross sectional views of the front end of the barrel and plunger of the device of FIG. 1 in operation.

As shown in FIGS. 2A,2B,2C, the forward end of barrel 10 has a relatively deep concave curved surface 26 and the forward end of plunger 12 normally has a relatively shallow convex curved surface 28. Both concave surface 26 and convex surface 28 are characterized by unreversed curves. More technically, intersections of each of these surfaces with a plane through their axis is a line extending rearwardly from its forward extremity with no point of inflection. In operation, as plunger 12 descends, successive increments of surface 28 contact successive corresponding increments of surface 26 along a circle 30 about the axis of the surfaces. And as plunger 12 ascends, successive increments of surface 28 separate from successive corresponding increments of surface 26 along circle 30. In consequence, fluid is inducted into specimen cavity 32 as an integral mass as the plunger ascends and is extruded from the specimen cavity completely as the plunger descends. Because suction and compression are bought to bear on the cervical mucus virtually in the absence of air and in a manner that precludes the trapping of mucus between the convex tip of the barrel and the concave tip of the plunger, even minute quantities of cervical mucus can be retrieved and extruded. In essence, cavity 32 can be constricted from a predetermined volume to virtually zero volume, the motion between the rigid surface of the barrel and the elastomeric surface of the plunger being peristaltic, i.e. being characterized by sequential increment to sequential increment rolling wavelike contact.

Figures 3A, 3B, 3C:
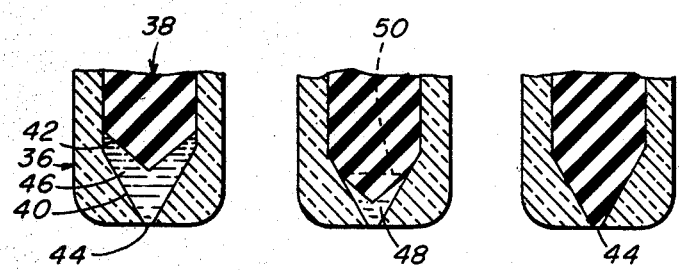
FIGS. 3A, 3B, 3C are a squence of cross sectional views of the front end of the barrel and the plunger of an alternative device embodying the present invention.

As shown in FIGS. 3A,3B,3C, the rigid forward end of a barrel 36 has a relatively deep concave conical surface 40 and the elastomeric forward end of a plunger 38 normally has a relatively shallow convex conical surface 42. Both concave surface 40 and the convex surface 42 are characterized in the same manner as surfaces 26, 28. More technically, the intersections of each of these surfaces with a plane through their axis is a line extending rearwardly from its forward extremity with no point of inflection. In operation, as plunger 38 descends, successive increments of surface 42 contact successive corresponding increments of surface 40 along a circle 50 about the axis of the surfaces. And as plunger 38 ascends, successive increments of surface 42 separate from successive corresponding increments of surface 40 along circle 50. In consequence, fluid is inducted into specimen cavity 46 as an integral mass as the plunger ascends and is extruded from the specimen cavity completely as the plunger descends. Because, suction and compression are bought to bear on the cervical mucus virtually in the absence of air and in a manner that precludes the trapping of mucus between the convex tip of the barrel and the concave tip of the plunger, even minute quantities of cervical mucus can be retrieved and extruded. In essence, cavity 48 can be constricted from a predetermined volume to virtually zero volume, the motion between the rigid surface of the barrel and the elastomeric surface of the plunger being peristaltic, i.e. being characterized by sequential increment to sequential increment rolling wave-like contact.

In operation, the sterilized replaceable barrel and plunger combination are inserted through mount 16 of handle 18 and the outwardly projecting rearward end of the plunger is affixed to a handle 24. Next, the forward extremity of barrel 10 is inserted through the vaginal cavity into contact with the cervical os. Next, handle 24 is withdrawn slightly in order to cause sufficient suction at aperture 14 for retrieval of cervical mucus. Then handles 24, 18 are pinched together and the entire device is removed from the vaginal cavity. Finally, handle 24 is advanced with respect to handle 18 in order to eject the speciment at the forward extremity of barrel 10 onto a test device.

The present invention thus provides an instrument by which even minute quantities of cervical mucus may be obtained in a sample for test purposes. Since certain changes may be made in the present disclosure without departing from the scope of the present invention, it is intended that all matter contained in the foregoing description or shown in the accompanying drawings be interpreted in an illustrative and not in a limiting sense.

What is claimed is:

1. A device for retrieving cervical mucus, said device comprising:
   (a) a first handle;
   (b) a second handle;
   (c) a barrel having a rigid main body configuration and a rigid forward tip configuration, said rigid main body configuration and said rigid forward tip configuration being substantially continuous with respect to each other, said barrel being affixed to said first handle;
   (d) a plunger having a resilient main body configuration and a resilient forward tip configuration, said resilient main body configuration and said resilient forward tip configuration being substantially continuous with respect to each other, said plunger being affixed to said second handle;
   (e) said plunger being reciprocable within said barrel and the general diameter of said rigid main body configuration and the general diameter of said resilient main body configuration being substantially the same;
   (f) the major portion of said rigid forward tip configuration of said barrel being relatively deep;
   (g) the major portion of said resilient forward tip configuration of said plunger being relatively shallow;
   (h) a cavity being defined between said resilient forward tip configuration of said plunger and said rigid forward tip configuration of said barrel such that, in a plane through the axis of said rigid tip configuration of said barrel and said resilient tip configuration of said plunger, a line at the surface of said resilient tip configuration of said plunger has no point of inflection and a line at the surface of said rigid tip configuration of said barrel has no point of inflection;
   (i) forward motion of said resilient forward tip configuration of said plunger with respect to said rigid forward tip configuration of said barrel sequentially causing contact between successive increments of said resilient forward tip configuration of said plunger and successive increments of said rigid forward tip configuration of said barrel;
(j) withdrawal of said resilient forward tip configuration of said plunger with respect to said rigid forward tip configuration of said barrel sequentially causing separation of successive increments of said resilient forward tip configuration of said plunger and successive increments of said rigid forward tip configuration of said barrel;
(k) whereby fluid in said cavity is maintained as an integral mass as it flows through said aperture;
(l) said cavity being variable between a positive volume and a substantialy zero volume.

2. The device of claim 1 wherein said forward tip configuration of said barrel is continuously concavely curved and said forward tip configuration of said plunger is continuously convexly curved.

3. The device of claim 1 wherein said forward tip configuration of said barrel is continuously concavely conical and said forward tip configuration of said plunger is continuously convexly conical.

* * * * *